(12) United States Patent
Mansfield

(10) Patent No.: US 10,391,002 B2
(45) Date of Patent: *Aug. 27, 2019

(54) STRETCH LAMINATE, METHOD OF MAKING, AND ABSORBENT ARTICLE

(71) Applicant: The Procter & Gamble Company, Cincinnati, OH (US)

(72) Inventor: Todd Leon Mansfield, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 782 days.

This patent is subject to a terminal disclaimer.

(21) Appl. No.: 15/060,941

(22) Filed: Mar. 4, 2016

(65) Prior Publication Data

US 2016/0184144 A1 Jun. 30, 2016

Related U.S. Application Data

(63) Continuation of application No. 13/895,403, filed on May 16, 2013, now Pat. No. 9,301,888, which is a
(Continued)

(51) Int. Cl.
*A61F 13/15* (2006.01)
*A61F 13/49* (2006.01)
(Continued)

(52) U.S. Cl.
CPC .. *A61F 13/49007* (2013.01); *A61F 13/15699* (2013.01); *A61F 13/49011* (2013.01);
(Continued)

(58) Field of Classification Search
CPC .......... A61F 13/15699; A61F 13/49011; A61F 13/49014; B32B 2307/54; B32B 5/022; B32B 5/26; B32B 7/12
See application file for complete search history.

(56) References Cited

U.S. PATENT DOCUMENTS 3,848,594 A  11/1974 Buell
3,860,003 A   1/1975 Buell
(Continued)

FOREIGN PATENT DOCUMENTS

EP  1261479 B1  12/2002
EP  1566475 A    8/2005
(Continued)

OTHER PUBLICATIONS

International Search Report, PCT/IB2007/051512, dated Apr. 29, 2008, 12 pages.
(Continued)

*Primary Examiner* — Peter S Vasat
(74) *Attorney, Agent, or Firm* — Christian M. Best; William E. Gallagher

(57) ABSTRACT

A stretch laminate includes a first layer including an elastomer film, the first layer having a surface, and a second layer including a nonwoven material, the second layer having a surface that is attached to the surface of the first layer. The tensile behavior in the transverse direction of the stretch laminate is within about 2.5 N/cm of the tensile behavior in the transverse direction of the film at an engineering strain of about 1.5, and exists independent of mechanical activation. A method of making the stretch laminate and an absorbent article having at least one region defined by the stretch laminate are also provided.

19 Claims, 3 Drawing Sheets

Related U.S. Application Data continuation of application No. 12/916,662, filed on Nov. 1, 2010, now Pat. No. 8,460,263, which is a continuation of application No. 11/410,170, filed on Apr. 24, 2006, now Pat. No. 7,833,211.

(51) Int. Cl.

| | | |
|---|---|---|
| *B32B 5/26* | (2006.01) | |
| *B32B 7/12* | (2006.01) | |
| *B32B 25/10* | (2006.01) | |
| *B32B 27/02* | (2006.01) | |
| *B32B 5/02* | (2006.01) | |
| *B32B 25/04* | (2006.01) | |
| *B32B 7/14* | (2006.01) | |
| *A61F 13/56* | (2006.01) | |
| *A61F 13/58* | (2006.01) | |

(52) U.S. Cl.
CPC ...... *A61F 13/49014* (2013.01); *A61F 13/565* (2013.01); *A61F 13/58* (2013.01); *B32B 5/022* (2013.01); *B32B 5/26* (2013.01); *B32B 7/12* (2013.01); *B32B 7/14* (2013.01); *B32B 25/045* (2013.01); *B32B 25/10* (2013.01); *B32B 27/02* (2013.01); *B32B 2262/02* (2013.01); *B32B 2262/04* (2013.01); *B32B 2262/06* (2013.01); *B32B 2266/025* (2013.01); *B32B 2266/0228* (2013.01); *B32B 2266/0278* (2013.01); *B32B 2266/06* (2013.01); *B32B 2266/08* (2013.01); *B32B 2307/54* (2013.01); *B32B 2307/726* (2013.01); *B32B 2555/02* (2013.01); *Y10T 156/10* (2015.01); *Y10T 428/2481* (2015.01); *Y10T 428/24826* (2015.01); *Y10T 428/24851* (2015.01); *Y10T 442/659* (2015.04); *Y10T 442/674* (2015.04); *Y10T 442/679* (2015.04)

(56) References Cited

U.S. PATENT DOCUMENTS

| | | |
|---|---|---|
| 3,911,173 A | 10/1975 | Sprague, Jr. |
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,662,875 A | 5/1987 | Hirotsu et al. |
| 4,673,402 A | 6/1987 | Weisman et al. |
| 4,695,278 A | 9/1987 | Lawson |
| 4,699,622 A | 10/1987 | Toussant et al. |
| 4,710,189 A | 12/1987 | Lash |
| 4,785,996 A | 11/1988 | Ziecker et al. |
| 4,795,454 A | 1/1989 | Dragoo |
| 4,808,178 A | 2/1989 | Aziz et al. |
| 4,834,735 A | 5/1989 | Alemany et al. |
| 4,842,666 A | 6/1989 | Werenicz |
| 4,846,815 A | 7/1989 | Scripps |
| 4,881,231 A | 11/1989 | Jain |
| 4,892,536 A | 1/1990 | DesMarais et al. |
| 4,894,060 A | 1/1990 | Nestegard |
| 4,909,803 A | 3/1990 | Aziz et al. |
| 4,940,464 A | 7/1990 | Van Gompel et al. |
| 4,964,527 A | 10/1990 | Martin |
| 4,968,312 A | 11/1990 | Khan |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,037,416 A | 8/1991 | Allen et al. |
| 5,062,480 A | 11/1991 | Chacin U. et al. |
| 5,092,861 A | 3/1992 | Nomura et al. |
| 5,116,662 A | 5/1992 | Morman |
| 5,137,537 A | 8/1992 | Herron et al. |
| 5,147,345 A | 9/1992 | Young et al. |
| 5,151,092 A | 9/1992 | Buell et al. |
| 5,167,897 A | 12/1992 | Weber et al. |
| 5,171,236 A | 12/1992 | Dreier et al. |
| 5,221,274 A | 6/1993 | Buell et al. |
| 5,246,433 A | 9/1993 | Hasse et al. |
| 5,260,345 A | 11/1993 | DesMarais et al. |
| 5,269,755 A | 12/1993 | Bodicky |
| 5,269,775 A | 12/1993 | Freeland et al. |
| 5,306,266 A | 4/1994 | Freeland |
| 5,342,338 A | 8/1994 | Roe |
| 5,387,207 A | 2/1995 | Dyer et al. |
| 5,397,318 A | 3/1995 | Dreier |
| 5,514,121 A | 5/1996 | Roe et al. |
| 5,527,304 A | 6/1996 | Buell et al. |
| 5,540,671 A | 6/1996 | Dreier |
| 5,554,142 A | 9/1996 | Dreier et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,653,703 A | 8/1997 | Roe et al. |
| H1732 H | 6/1998 | Johnson |
| 5,851,935 A | 12/1998 | Srinivasan et al. |
| 5,853,881 A | 12/1998 | Estey et al. |
| 5,865,823 A | 2/1999 | Curro |
| 5,897,545 A | 4/1999 | Kline et al. |
| 5,938,648 A | 8/1999 | LaVon et al. |
| 5,941,864 A | 8/1999 | Roe |
| 5,957,908 A | 9/1999 | Kline et al. |
| 5,968,025 A | 10/1999 | Roe et al. |
| 5,977,430 A | 11/1999 | Roe et al. |
| 5,997,520 A | 12/1999 | Ahr et al. |
| 6,004,306 A | 12/1999 | Robles et al. |
| 6,010,490 A | 1/2000 | Freeland et al. |
| 6,013,063 A | 1/2000 | Roe et al. |
| 6,069,097 A | 5/2000 | Suzuki et al. |
| 6,120,487 A | 9/2000 | Ashton |
| 6,120,489 A | 9/2000 | Johnson et al. |
| 6,168,584 B1 | 1/2001 | Allen et al. |
| 6,313,372 B1 | 11/2001 | Suzuki |
| 6,383,431 B1 | 5/2002 | Dobrin et al. |
| 6,428,526 B1 | 8/2002 | Heindel et al. |
| 6,432,098 B1 | 8/2002 | Kline et al. |
| 6,537,930 B1 | 3/2003 | Middlesworth et al. |
| 6,582,414 B1 | 6/2003 | Richardson |
| 6,680,422 B2 | 1/2004 | Roe |
| 6,716,441 B1 | 4/2004 | Osborne et al. |
| 7,150,732 B2 | 12/2006 | Yoshida et al. |
| 7,329,621 B2 | 2/2008 | Collier, IV et al. |
| 7,351,296 B2 | 4/2008 | Waggoner et al. |
| 7,829,487 B2 | 11/2010 | Suzuki et al. |
| 7,833,211 B2 * | 11/2010 | Mansfield ......... A61F 13/49011 604/385.22 |
| 7,910,658 B2 | 3/2011 | Chang et al. |
| 8,292,865 B2 | 10/2012 | Hutson et al. |
| 8,460,263 B2 * | 6/2013 | Mansfield ......... A61F 13/49011 604/385.22 |
| 9,301,888 B2 * | 4/2016 | Mansfield ......... A61F 13/49011 |
| 2003/0054720 A1 | 3/2003 | Ohwada et al. |
| 2003/0060794 A1 | 3/2003 | Olson |
| 2003/0091807 A1 | 5/2003 | Desai et al. |
| 2003/0124306 A1 | 7/2003 | Morman |
| 2003/0153894 A1 * | 8/2003 | Gibbs ............... A61F 13/15203 604/386 |
| 2003/0207640 A1 | 11/2003 | Anderson et al. |
| 2004/0112524 A1 | 4/2004 | Erdos et al. |
| 2004/0222553 A1 | 11/2004 | Desai et al. |
| 2005/0158513 A1 | 7/2005 | Peacock et al. |

(56) References Cited

U.S. PATENT DOCUMENTS

| | | |
|---|---|---|
| 2005/0222546 A1 | 10/2005 | Vargo et al. |
| 2005/0244619 A1 | 11/2005 | Kauschke et al. |
| 2006/0003658 A1 | 1/2006 | Hall et al. |
| 2006/0052023 A1 | 3/2006 | Lauridsen et al. |
| 2006/0083898 A1 | 4/2006 | Deng et al. |
| 2007/0144660 A1 | 6/2007 | O'Sickey et al. |
| 2007/0202767 A1 | 8/2007 | Anderson et al. |
| 2007/0249254 A1 | 10/2007 | Mansfield |
| 2007/0293111 A1 | 12/2007 | Mansfield |
| 2011/0066126 A1 | 3/2011 | Mansfield |

FOREIGN PATENT DOCUMENTS

| | | |
|---|---|---|
| JP | 10-195746 A | 7/1998 |
| JP | 2004-098356 | 4/2004 |
| WO | WO 95/16746 | 6/1995 |
| WO | WO 01/73174 | 10/2001 |

OTHER PUBLICATIONS

Product specification of FPN 332D, dated Oct. 12, 2014 (1 page).
Phyical Properties of Textile Fibres, 1993, p. 674; North & Hearle (3 pages).
All Office Actions, U.S. Pat. No. 7,833,211.
All Office Actions, U.S. Pat. No. 8,460,263.
All Office Actions, U.S. Pat. No. 9,301,888.

* cited by examiner

STRETCH LAMINATE, METHOD OF MAKING, AND ABSORBENT ARTICLE

CROSS REFERENCE TO RELATED APPLICATION

This application is a continuation of application Ser. No. 13/895,403, filed May 16, 2013, which is a continuation of application Ser. No. 12/916,662 (now U.S. Pat. No. 8,460,263 B2), filed Nov. 1, 2010, which is a continuation of application Ser. No. 11/410,170 (now U.S. Pat. No. 7,833,211 B2), filed Apr. 24, 2006, the substances of which are incorporated herein by reference.

FIELD OF THE INVENTION

The present disclosure generally relates to a stretch laminate and a method of making the same, and to an absorbent article, such as a diaper, a pant, or the like, made using the stretch laminate.

BACKGROUND OF THE INVENTION

Disposable absorbent articles, such as diapers, are designed to contain bodily exudates, such as urine, to prevent the soiling of the wearer's clothing and/or other items (e.g., a bed, a chair, a blanket, etc.). The fit of the article to the wearer's body is important in ensuring that these wastes are contained, instead of leaking out. The fit of the article to the wearer's body may be affected by the size of the diaper waist opening, the size of the openings around the thighs, and the length or "pitch" of the diaper.

Disposable absorbent articles are also designed to be cost-effective. That is, the average consumer may have second thoughts about using a product that holds itself out as disposable if the cost per article is too high. Thus, manufacturers generally make such articles for use by individuals with a wide range of body types that may be classified by a broad criterion, such as weight, for example.

It will be recognized that the need to make products that conform to a wide range of body types competes with the desire for the article to fit snuggly to the user to contain wastes and limit leakage.

One way in which manufacturers attempt to balance the competing interests of proper fit and variation in body type is through the use of expandable materials. One such group of materials is known as stretch laminates. As the name suggests, these materials are actually composites of individual components that are laminated together, through the use of an adhesive, for example. A typical stretch laminate will attempt to combine an inner layer defined by a material having good elasticity, to accommodate varying body types, with outer layers defined by a fabric-like material, to accommodate user expectations for look and feel.

A complication arises in that these stretch laminates are notoriously difficult to manufacture. Considerable effort has gone into proposing new methods for the fabrication of stretch laminates. In particular, a considerable number of patents discuss the difficulties of fabricating these laminates, and the significant and extensive steps that must be undertaken to prepare these laminates. Certain patents recommend that steps to be taken before lamination, such as "neck bonded laminates." Other patents recommend that steps to be taken after lamination, such as "activating" in ring rolls. Still other patents recommend special handling of the inner layer as part of the lamination process, such as holding the inner layer in a stretched configuration during the lamination. Concomitant with such significant and extensive pre-processing, post-processing or handling steps are significant fabrication costs.

Thus, it would be desirable to provide new stretch laminates and methods for making stretch laminates. In particular, it would be desirable to provide less expensive laminates produced by simpler fabrication methods.

SUMMARY OF THE INVENTION

In one aspect, a stretch laminate comprises a first layer comprising an elastomer film, the first layer having a surface, and a second layer comprising a nonwoven material, the second layer having a surface that is attached to the surface of the first layer. The tensile behavior in the transverse direction of the stretch laminate is within about 2.5 N/cm of the tensile behavior in the transverse direction of the film at an engineering strain of about 1.5, and exists independent of mechanical activation.

In another aspect, a method of making a stretch laminate is provided, the method consisting essentially of providing an elastomer film, and attaching a nonwoven layer to the elastomer film. The tensile behavior in the transverse direction of the stretch laminate so made is within about 2.5 N/cm of the tensile behavior in the transverse direction of the film at an engineering strain of about 1.5, and exists independent of mechanical activation.

In a further aspect, an absorbent article having a waist region and a crotch region is provided, the article comprising a backsheet having a longitudinal axis, a topsheet attached to the backsheet and having a body-facing surface, an absorbent core disposed between the backsheet and the topsheet, and a stretch laminate defining at least one region of the absorbent article. The stretch laminate comprises a first layer comprising an elastomer film, the first layer having a surface, and a second layer comprising a nonwoven material, the second layer having a surface that is attached to the surface of the first layer. The tensile behavior in the transverse direction of the stretch laminate is within about 2.5 N/cm of the tensile behavior in the transverse direction of the film at an engineering strain of about 1.5, and exists independent of mechanical activation.

Additional aspects of the disclosure are defined by the claims of this patent.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Definitions

Figure 1A:
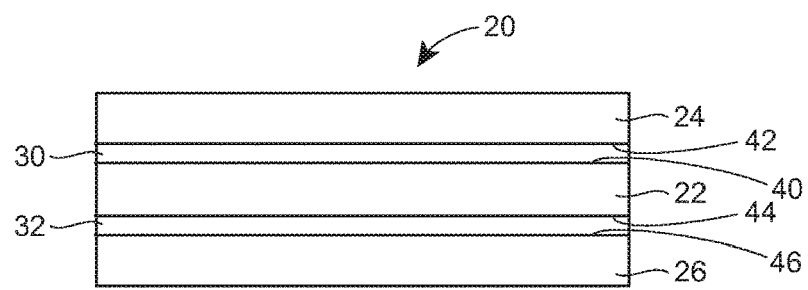
FIG. 1A is a side view of a first embodiment of a stretch laminate according to the present disclosure.

As used herein, the following terms have the following meanings:

The term "absorbent article" refers to a device that absorbs and contains liquid, and more specifically, refers to a device that is placed against or in proximity to the body of the wearer to absorb and contain the various exudates discharged from the body.

The terms "adhesively bonded" or "adhesively laminated" refers to a laminate wherein an adhesive is used to bond the elastic member to the nonwoven or nonwovens.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "diaper" refers to an absorbent article generally worn by infants and incontinent persons about the lower torso and having the general form of a sheet, different portions of which are fastened together to encircle the waist and the legs of the wearer.

The term "disposable" refers to absorbent articles that generally are not intended to be laundered or otherwise restored or reused as absorbent articles, i.e., they are intended to be discarded after a single use and, preferably, to be recycled, composted or otherwise disposed of in an environmentally compatible manner.

The term "disposed" is used to mean that an element(s) is formed (joined and positioned) in a particular place or position as a unitary structure with other elements or as a separate element joined to another element.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower" and "top" and "bottom", respectively.

The term "joined" refers to configurations whereby an element is directly secured to another element by attaching the element directly to the other element, and configurations whereby an element is indirectly secured to another element by attaching the element to intermediate member(s) which in turn are attached to the other element.

The term "lateral" or "transverse" refers to a direction running at a 90 degree angle to the longitudinal direction and includes directions within ±45° of the lateral direction.

The term "longitudinal" refers to a direction running parallel to the maximum linear dimension of the article and includes directions within ±45° of the longitudinal direction.

The term "macroporous" refers to materials having pores too large to effect capillary transport of fluid, generally having pores greater than about 0.5 mm in diameter and, more specifically, having pores greater than about 1.0 mm in diameter. The term "microporous" refers to materials which are capable of transporting fluids by capillary action.

The term "pant" or "pants" refers to an absorbent article generally worn by infants and incontinent persons about the lower torso and having the general form of a pair of short pants that can be applied or removed from the wearer without unfastening. A pant may be placed in position on the wearer by inserting the wearer's legs into the leg openings and sliding the pant into position about the wearer's lower torso. While the term "pant" is used herein, pants are also commonly referred to as "closed diapers", "prefastened diapers", "pull-on diapers", "training pants" and "diaper-pants".

The term "refastenable" refers to the property of two elements being capable of releasable attachment, separation, and subsequent releasable reattachment without substantial permanent deformation or rupture.

The terms "releasably attached," "releasably engaged," and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

Stretch Laminate and Method of Fabrication

Figure 1B:
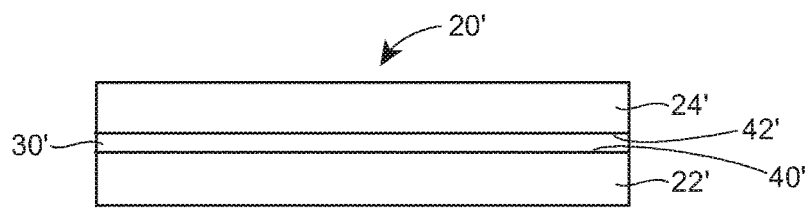
FIG. 1B is a side view of a second embodiment a stretch laminate according to the present disclosure.

FIG. 1A illustrates an embodiment of a stretch laminate 20 according to the present disclosure. According to this embodiment, the laminate 20 may include three layers: a first, or inner, layer 22 and second and third, or outer, layers 24, 26. However, according to other embodiments, the laminate 20' may include only two layers, the first and second layers 22', 24', as shown in FIG. 1B.

The first, second and third layers 22, 24, 26 may be attached to each other. For example, an adhesive may be disposed between the layers 22, 24, 26, as shown at 30, 32. As will be recognized, the adhesive 30 may be initially disposed either on a surface 40 of the layer 22 or a surface 42 of the layer 24, and the adhesive 32 may be similarly initially disposed either on an opposite surface 44 of the layer 22 or a surface 46 of the layer 26. As assembled, the adhesive 30 attaches the surface 40 (and thus the layer 22) to the surface 42 (and thus the layer 24), and the adhesive 32 attaches the surface 44 (and thus the layer 22) to the surface 46 (and thus the layer 26).

While the layers 22, 24, 26 appear to overlie each other completely, this need not be the case in all embodiments. For example, the layers 24, 26 may extend beyond the layer 22, and may be attached one to the other where the layers 24, 26 extend beyond the layer 22; alternatively, the layers 24, 26 may not extend to the limits of the layer 22. Also, while the adhesive 30, 32 appears as a continuous layer in the Figure, the adhesive 30, 32 may be applied as a continuous layer or in a discontinuous pattern (such as a pattern of lines, spirals, or spots). Further, alternative attachment mechanisms may include heat bonding, pressure bonding, ultrasonic bonding, dynamic mechanical bonding, or any other suitable attachment mechanism or combinations of these attachment mechanisms.

According to the present disclosure, the inner layer 22, or core, may include an elastomer film. Exemplary elastomer films may include M18-1117 and M18-1361 elastomer film commercially available from Clopay Corporation of Cincinnati, Ohio and K11-815 and CEX-826 elastomer film commercially available from Tredegar Film Products of Richmond, Va. Such materials are believed to have good elasticity properties. Exemplary elastomer films may include those with skins, and those that are skinless.

The outer layers 24, 26 may be of a nonwoven material, such as SM (spunbond meltblown), SMS (spunbond meltblown spunbond), and SMMS (spunbond meltblown meltblown spunbond) nonwovens. According to the present disclosure, the nonwovens may have low TD (transverse direction) tensile forces. In particular, according to an embodiment, the tensile force of the laminate 20 is preferably within about 2.5 N/cm of the tensile force of the inner layer 22 alone. Specific nonwovens that meet this criterion may include CS9520001 (25 gsm) nonwovens commercially available from Advanced Design Concepts (ADC), a joint venture of The Dow Chemical Co. and BBA Group PLC, of Brentwood, Tenn. and TS4288-2 (49 gsm) and TS4288-6 (53 gsm) nonwovens from Kuraray America Inc. of New York, N.Y. According to another embodiment, the tensile force of the laminate 20 is preferably within about 1 N/cm of the tensile force of the inner layer 22 alone. Specific nonwovens that meet this criterion may include the CS9520001 ADC (25 gsm) nonwovens and the TS4288-6 Kuraray (53 gsm) nonwovens. Whether this criterion is met, either at the 2.5 N/cm level or the 1 N/cm level, may be determined at an engineering strain of about 1.5.

It also may be desirable, according to certain embodiments, for the laminate 20 and/or the inner layer 22 to have a particular energy recovery value. According to this disclosure, the energy recovery value is a value that is associated with energy expended and recovered during loading and unloading of a material. According to one embodiment, for engineering strains at least between 50% and 250%, the inner layer material may have an energy recovery value of about 0.1 or greater, and the laminate 20 should may an energy recovery value within the range of about 0.1 or greater.

The adhesive 30, 32 may be selected from those adhesives known to provide suitable attachment between the film 22 and the nonwoven layers 24, 26. According to one embodiment, the adhesive may be the H2031 adhesive commercially available from Bostik Inc. of Middleton, Mass. One characteristic of this adhesive is that, at 23 C, this adhesive has significant pressure-sensitive character useful for making laminate by hand. However, this adhesive is also suitable for use in fabricating laminates from the films and nonwovens listed above using conventional laminate manufacturing equipment, such equipment being well known in the art.

An exemplary method of fabricating a laminate using the films, nonwovens and adhesives listed above is as follows. Adhesive 30 may be applied to release paper in a spiral pattern (9.3 gsm). The adhesive 30 may then be transferred to one side 40 of the film 22 by placing the sheet of film 22 on the adhesive 30, and then applying sufficient pressure to the film 22, with a hand roller, for example, so the adhesive 30 would transfer from the release paper to the surface 40 of the film 22, then gradually peeling the release paper from the adhesive 30. The nonwoven layer 24 may then be applied to the adhesive 30. This procedure may then be repeated to attach the other surface 44 of the film 22 to the surface 46 of the nonwoven layer 26 using the adhesive 32. Once the layers 22, 24, 26 are assembled, a hand roller, for example, may be used to apply moderate pressure to the laminate 20 to give laminate 20 adequate peel strength (approximately 0.5 N/cm). According to this exemplary embodiment, the layers 22, 24, 26 are assembled so that the direction of the film 22 and the direction of the nonwoven layers 24, 26 coincide. It will be recognized that these steps may be performed on conventional fabrication equipment, according to the knowledge of those of skill in the art.

The above-mentioned method of making the laminate has several advantages. There is no pre-processing step required to prepare the materials for lamination. For example, no special handling of the elastomer film is required: the adhesives are applied and the materials combined without any forces being applied to the materials to keep them in an elongated state, or any other state. Additionally, there is no post-processing step required to prepare the laminate for use. Stated another way, the laminate may exhibit, for example, the tensile behavior noted above independent of any mechanical activation of the laminate or its constituents.

Testing Methods and Results

Exemplary methods of testing the inner layer materials and laminate materials to determine if they meet the tensile force and energy recovery value criteria follow.

The exemplary methods of testing for both the tensile force and energy recovery value criteria were performed using an Alliance RT/1 tensile testing system, commercially available from MTS Systems Corporation of Eden Prairie, Minn. According to the exemplary testing methods, the Alliance RT/1 tensile testing system was fitted out with a set of custom fabricated grips. The grips have opposing rubber faces that are brought together using a screw-action clamp, and provide line contact. Suitable alternative grips may include MTS part numbers 056-163-829 (line contact grip faces) and 100-036-576 (pneumatically actuated grips). Regardless of the grips selected, it is preferred that the specimen is mounted in the grips so that slippage or damage is limited, most preferably so that no appreciable slippage or damage occurs. For example, the specimen is mounted with good alignment and with limited (most preferably, no appreciable) slack or stretching. It is believed that such mounting will provide well-defined lines of contact on the specimen.

The specimens may be prepared for testing according to the exemplary testing methods according to the following procedure. A sharp blade, such as an XACTO knife commercially available from Hunt Corporation of Philadelphia, Pa., and a metal straight edge may be used to cut a specimen that is 19 mm wide by approximately 30 mm long. The specimen's long dimension may be measured with a scale to the nearest 0.2 mm and weighed on a four-place lab balance. The 30 mm dimension was selected to coincide with the specimen's transverse direction (also known as the cross-machine direction). The specimen may be mounted at an initial grip position of 25.4 mm.

An exemplary method of testing a sample of a laminate to determine if the tensile force criterion is met is as follows, although other methods may be used. For the purposes of this testing, the Alliance RT/1 system is operated with a load cell selected according to the operator's experience and according to the parameters listed below:

ambient temperature: 23 C;
stretching direction: TD (transverse direction);

gauge length: 25.4 mm; and
crosshead speed: 4.23 mm/s (10 inches/min.).
Further, multiple specimens may be run for each inner layer material or laminate material tested.

An exemplary method of testing a sample of a material to determine if the energy recovery value criterion is met is as follows, although other methods may be used. For the purposes of this testing, the Alliance RT/1 system is operated with a load cell selected according to the operator's experience and according to the parameters listed below:
number of stretch/unstretch cycles: 1;
ambient temperature: 23 C;
stretching direction: TD (transverse direction);
gauge length: 25.4 mm;
crosshead speed: 4.23 mm/s (10 inches/min.); and
maximum extension: 50%, 150%, 200%, 250% or 350%.
Further, the table below summarizes the displacement regimen carried out for an extension of 200%; modifications necessary for other extensions (e.g., 50%, 150%, 250%, 350%) will be apparent to those skilled in the art.

Displacement Regimen

| Step | z start (mm) | z end (mm) | L start (mm) | L end (mm) | e start (unitless) | e end (unitless) | Speed (mm/s) | Hold time(s) |
|---|---|---|---|---|---|---|---|---|
| mount | 0 | 0 | 25.4 | 25.4 | 0 | 0 | N/A | N/A |
| pre-jog | 0 | −5 | 25.4 | 20.4 | 0 | slack | non-critical | N/A |
| load | −5 | 50.8 | 20.4 | 76.2 | slack | 2 | 4.23 | N/A |
| hold | 50.8 | 50.8 | 76.2 | 76.2 | 2 | 2 | 0 | 30 |
| unload | 50.8 | −5 | 76.2 | 20.4 | 2 | slack | 4.23 | N/A |

It will be recognized that the pre-jog step is optional, but may be included to allow the crosshead to come up to speed before tensile deformation of the specimen begins. It will also be recognized that e (engineering strain) is defined as:

$$e=(L-L_0)/L_0=z/L_0$$

where $L_0$ (gauge length) is the distance between lines of grip contact when the undeformed specimen is mounted in the grips (i.e., $L_0$ is 25.4 mm); L (grip position) is the distance between lines of grip contact during the test; and z (displacement) is the difference between L and $L_0$. Here as well, multiple specimens may be run for each inner layer material or laminate material tested.

As for the determination of the energy recovery values, the tensile forces measured during the testing may be plotted relative to displacement. The area under the graph for values measured during loading represents the energy of loading. Similarly, the area under the graph for values measured during unloading represents the energy of unloading. The ratio of the energy of unloading to the energy of loading may define the energy recovery value (ERV). Another way to express the relationship is as follows:

$$ERV=\int Fdz(\text{unload})/\int Fdz(\text{load});$$

where F and z are force and displacement, respectively, and the integral in the numerator is evaluated for the "unload" step and the integral in the denominator is evaluated for the "load" step.

Tensile Force Results

Nine different laminates were tested for tensile force. The laminates had three layers, an inner layer defined by an elastomer film and two outer layers defined by a nonwoven. The following commercially-available elastomers were used: M18-1117 elastomer commercially available from Clopay Corporation of Cincinnati, Ohio (film 1); K11-815 elastomer commercially available from Tredegar Film Products of Richmond, Va. (film 2); M18-1361 elastomer commercially available from Clopay Corporation (film 4); and CEX-826 elastomer commercially available from Tredegar Film Products (film 5).

Additionally, another elastomer film (film 3) was used, the film being prepared according to the following method: An UltraGlide twin screw extruder, commercially available from Berstorff GmbH of Hannover, Germany (with 25.4 mm diameter and L:D=32), was used to form the film using a 280-041 resin commercially available from GLS Composites Distribution Group of McHenry, Ill. The extruder was fitted with a vibratory feeder to deliver the resin pellets to the extruder's feed throat at a constant rate. The extrusion temperatures were set at 350° F. for the first extrusion zone and 400° F. for the last extrusion zone and the die, and selected for the middle zones to give a suitable upward temperature ramp profile. The screw speed was 100 rpm. The extruder was fitted with a 6 inch (15.2 cm) wide film die, and the film was cast directly onto release paper on a suitable film take-up apparatus.

The laminates were formed using CS9520001 (25 gsm) nonwoven from Advanced Design Concepts of Brentwood, Tenn. (nonwoven A), TS4288-2 (49 gsm) nonwoven commercially available from Kuraray America Inc. of New York, N.Y. (nonwoven B), TS4288-6 (53 gsm) nonwoven from Kuraray (nonwoven C), FPN332d (27 gsm) nonwoven from BBA Group PLC (nonwoven F), and COLI401473 (17 gsm) nonwoven from Corovin GmbH of Germany (nonwoven G).

Figure 2:
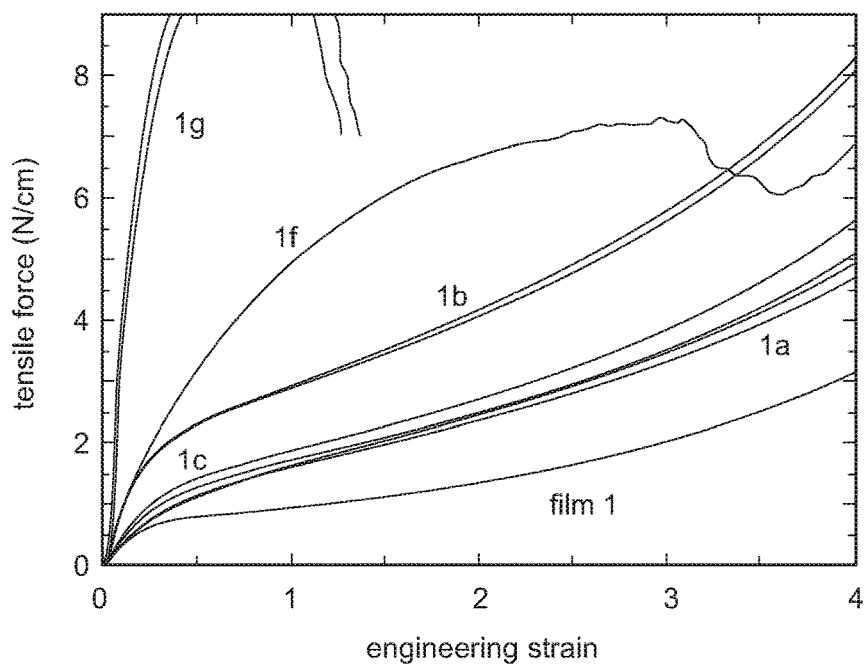
FIG. 2 is a graph illustrating results of testing performed on specimens to determine if they meet a tensile strength criteria set for a stretch laminate of FIGS. 1A, 1B.

Partial results of the testing, with tensile force plotted relative to engineering strain, are shown in FIG. 2. Each laminate is represented by a 2-character alphanumeric code, with the first character indicating the film used (1) and the second character indicating the nonwoven used (A, B, C, F, G). The results for the remaining specimens are provided below.

As seen in FIG. 2, at an engineering strain of about 1.5, the laminates using film 1 and nonwovens A and C have a tensile force that differs from the tensile force of the elastomer by about less than 1 N/cm. In the case of nonwoven A, the difference is about 0.88, while for nonwoven C, the difference is about 1.03. As for a laminate of film 1 and nonwoven B, the difference is about 2.34. All of three laminates are believed to provide suitable look and feel for use as a cloth-like material.

Additionally, testing with laminates of films 2-5 and nonwoven A resulted in laminates with suitable look and feel that satisfy the tensile force criteria set about above. That is, specimens of laminates of films 2-5 and nonwoven A exhibit the following differences between tensile force of the laminate and the tensile force of the film at an engineering strain of about 1.5: for 2 A, 0.72; for 3 A, 0.77; for 4 A, 0.59; and for 5 A, 0.84.

By contrast, the laminate of film 1 and nonwoven F has a much larger difference between the tensile force of the laminate and the elastomer (4.97 N/cm) at an engineering strain of about 1.5. Also, the laminate of film 1 and nonwoven G failed at the engineering strain used for the testing. Both of these laminates are believed not to provide suitable look and feel for use as a cloth-like material.

The following is a summary of the tensile strengths for the elastomer films and laminates at an engineering strain of about 1.5, as well as the differences:

Tensile Strength Results

| Laminate Identifier | Tensile Strength Laminate (N/cm) | Tensile Strength Film (N/cm) | Difference Tensile Strength (N/cm) |
| --- | --- | --- | --- |
| 1A | 1.99 | 1.12 | 0.88 |
| 1B | 3.46 | 1.12 | 2.34 |
| 1C | 2.15 | 1.12 | 1.03 |
| 1F | 6.09 | 1.12 | 4.97 |
| 2A | 1.90 | 1.18 | 0.72 |
| 3A | 1.57 | 0.80 | 0.77 |
| 4A | 1.53 | 0.94 | 0.59 |
| 5A | 1.77 | 0.93 | 0.84 |

Energy Recovery Value Results

Eight different laminates were tested for energy recovery value. The laminates had three layers, an inner layer defined by an elastomer film and two outer layers defined by a nonwoven. Also, the elastomer films were tested separately.

The following elastomers were used: M18-1117 elastomer commercially available from Clopay Corporation (film 1); K11-815 elastomer commercially available from Tredegar Film Products (film 2); an elastomer film prepared according to the method above (film 3); M18-1361 elastomer commercially available from Clopay Corporation (film 4); and CEX-826 elastomer commercially available from Tredegar Film Products (film 5).

The laminates were formed using CS9520001 (25 gsm) nonwoven from Advanced Design Concepts (nonwoven A), TS4288-2 (49 gsm) nonwoven commercially available from Kuraray America Inc. (nonwoven B), TS4288-6 (53 gsm) nonwoven from Kuraray (nonwoven C), and FPN332d (27 gsm) nonwoven from BBA Group PLC (nonwoven F).

For each film, the testing was performed at engineering strains of 150%, 200%, 250%, and/or 350%. For the laminates, the testing was performed at engineering strains of 50%, 150%, 250%, and/or 350%.

The results of the testing are summarized in the following tables. The first table includes results from the testing on the films separately. The second table (in two parts) includes results from the testing on the laminates, with each laminate represented by a 2-character alphanumeric code, with the first character indicating the film used (1, 2, 3, 4, 5) and the second character indicating the nonwoven used (A, B, C, F).

Film ERV Results

| engineering strain (unitless) | ERV film 1 (unitless) | ERV film 2 (unitless) | ERV film 3 (unitless) | ERV film 4 (unitless) | ERV film 5 (unitless) |
| --- | --- | --- | --- | --- | --- |
| 150 | 0.59 | 0.61 | not tested | not tested | not tested |
| 200 | 0.59 | 0.61 | 0.88 | 0.54 | 0.12 |
| 250 | 0.57 | 0.60 | not tested | not tested | not tested |
| 350 | 0.42 | 0.43 | not tested | not tested | not tested |

Laminate ERV Results (part 1)

| engineering strain (unitless) | 1A Laminate ERV (unitless) | 1B Laminate ERV (unitless) | 1C Laminate ERV (unitless) | 1F Laminate ERV (unitless) |
| --- | --- | --- | --- | --- |
| 50 | 0.47 | not tested | not tested | 0.20 |
| 150 | 0.43 | 0.44 | 0.60 | 0.17 |
| 250 | 0.40 | 0.41 | 0.60 | not tested |
| 350 | 0.30 | 0.32 | 0.45 | not tested |

Laminate ERV Results (part 2)

| engineering strain (unitless) | 2A Laminate ERV (unitless) | 3A Laminate ERV (unitless) | 4A Laminate ERV (unitless) | 5A Laminate ERV (unitless) |
| --- | --- | --- | --- | --- |
| 50 | not tested | 0.68 | 0.45 | 0.17 |
| 150 | 0.49 | 0.57 | 0.43 | 0.14 |
| 250 | 0.45 | 0.54 | 0.42 | 0.12 |
| 350 | 0.32 | 0.34 | 0.28 | 0.11 |

Exemplary Absorbent Article

Having thus described the stretch laminate according to the present disclosure and methods for its fabrication and testing, the use of the stretch laminate in an absorbent article is now discussed. While the use of the stretch laminate is suggested in regard to certain regions of the absorbent article, it will be recognized that the stretch laminate may be used in other regions as well.

Figure 3:
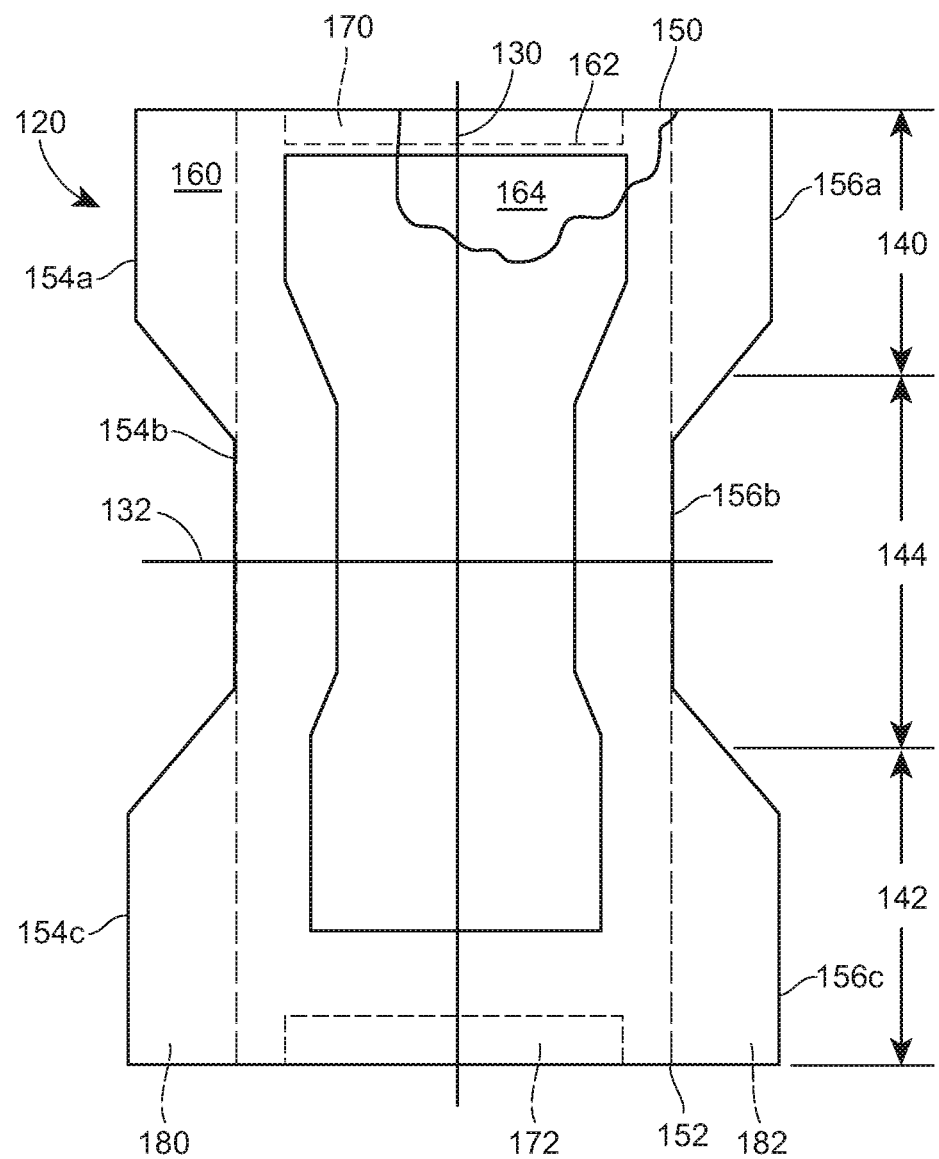
FIG. 3 is a plan view of an exemplary absorbent article including sections made of the stretch laminate of FIGS. 1A, 1B, with a section of a topsheet removed to expose an underlying absorbent core.

FIG. 3 is a plan view of an exemplary disposable absorbent article 120 in its flat, uncontracted state, i.e., without elastic-induced contraction. Portions of the article 120 have been cut away to more clearly show the underlying structure of the disposable absorbent article 120. As illustrated, the portion of the disposable absorbent article 20 that contacts the wearer faces the viewer (i.e., showing the interior or inner side of the article). The disposable absorbent article 120 has a longitudinal axis 130 and a transverse axis 132.

One end portion of the disposable absorbent article 120 is configured as a first waist region 140 of the disposable absorbent article 120. The opposite end portion is configured as a second waist region 142 of the disposable absorbent article 120. The waist regions 140 and 142 generally comprise those portions of the disposable absorbent article 120 which, when worn, encircle the waist of the wearer. The waist regions 140 and 142 may include elastic elements such that they gather about the waist of the wearer to provide improved fit and containment. An intermediate portion of the disposable absorbent article 120 is configured as a crotch region 144, which extends longitudinally between the first and second waist regions 140 and 142. The crotch region 144 is that portion of the disposable absorbent article 120 which, when the disposable absorbent article 120 is worn, is generally positioned between the legs of the wearer.

The disposable absorbent article 120 has a laterally extending first waist edge 150 in the first waist region 140 and a longitudinally opposing and laterally extending second waist edge 152 in the second waist region 142. The disposable absorbent article 120 has a first side edge 154 and a laterally opposing second side edge 156, both side edges extending longitudinally between the first waist edge 150 and the second waist edge 152. The portion of the first side edge 154 in the first waist region 140 is designated 154a, the portion in the crotch region 144 is designated 154b, and the portion in the second waist region 142 is designated 154c. The corresponding portions of the second side edge 156 are designated 156a, 156b, and 156c, respectively.

The disposable absorbent article 120 preferably comprises a water-permeable topsheet 160, a water-impermeable backsheet 162, and an absorbent assembly or core 164, which may be disposed between the topsheet 160 and the backsheet 162 with the topsheet 160 attached to the backsheet 162. The topsheet 160 may be fully or partially elasticized or may be foreshortened. Exemplary structures including elasticized or foreshortened topsheets are described in greater detail in U.S. Pat. Nos. 4,892,536; 4,990,147; 5,037,416; and 5,269,775, among others.

The absorbent article 120 may include at least one elastic waist feature 170 that helps to provide improved fit and containment. The elastic waist feature 170 may be intended to elastically expand and contract to dynamically fit the wearer's waist. The elastic waist feature 170 may extend at least longitudinally outwardly from at least one waist edge (e.g., edge 150) of the absorbent article 150 and generally forms at least a portion of the waist region (e.g., region 140) of the absorbent article 120. Diapers are often constructed so as to have two elastic waist features 170, 172, one (170) positioned in the first waist region 140 and one (172) positioned in the second waist region 142. Further, the elastic waist feature 170, 172 may be made of the stretch laminate 20 attached or joined to the backsheet 162. Alternatively, the elastic waist feature 170, 172 may be constructed as an extension of other elements of the absorbent article, such as the topsheet 160, the backsheet 162, or both the topsheet 160 and the backsheet 162 (e.g., the topsheet 160 or backsheet 162 defines one of the layers 24, 26 of the laminate 20). Other elastic waist feature constructions are described in U.S. Pat. Nos. 4,515,595; 4,710,189; 5,151,092; and 5,221,274.

The absorbent article 120 may include side panels 180, 182 attached to the backsheet 162. One or more of the side panels 180, 182 may be made from the stretch laminate 20. This construction may provide a more comfortable and contouring fit by initially conformably fitting the absorbent article 120 to the wearer, and sustaining this fit throughout the time of wear well past when the absorbent article 120 has been loaded with exudates, insofar as the elasticized side panels 180, 182 allow the sides of the absorbent article 120 to expand and contract. The side panels 180, 182 may also provide more effective application of the absorbent article 120 because even if the caretaker pulls one elasticized side panel 180 farther than the other (182) during application, the absorbent article 120 will "self-adjust" during wear. While the absorbent article 120 preferably has the side panels 180, 182 disposed in the second waist region 142, the absorbent article 120 may be provided with side panels disposed in the first waist region 140, or in both the front waist region 140 and the second waist region 142.

Figure 4:
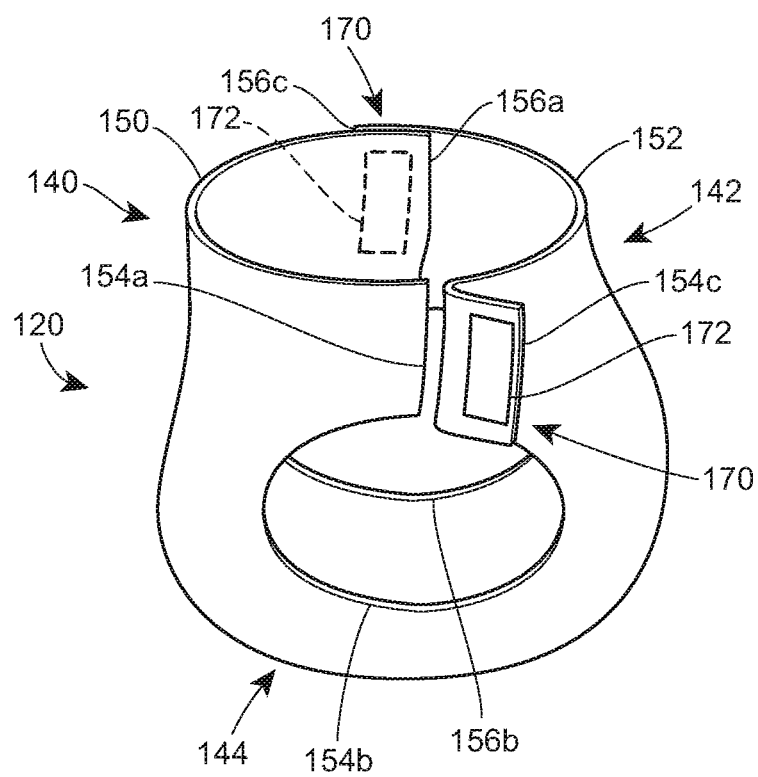
FIG. 4 is a perspective view of the absorbent article of FIG. 3 shown in its relaxed, contracted state, i.e., with the contraction induced by elastic members.

FIG. 4 illustrates the article illustrated in FIG. 3 configured to as it would be worn. The disposable absorbent article 120 may be sealed at the sides so as to be configured as illustrated in FIG. 3. However, the article 120 may instead include refastenable side seams 170 that can be used to fasten the waist regions 140, 142 together. According to one exemplary embodiment, the waist regions 140, 142 may be fastened at the sides to apply the article like a diaper. According to an exemplary embodiment, illustrated in FIG. 3, the side seams 170 may include fasteners 172 that can be used to configure the article like a pair of pull-on training pants or disposable pants.

As illustrated, the fasteners 172 may be disposed on the interior of the disposable absorbent article 120 in the second waist region 142 adjacent to the portion 154c of the first side edge 154 and adjacent to the portion 156c of the second side edge 156. The portion 154c of the side edge 154 is shown in an open condition, such as prior to closing and fastening or after being reopened. The portion 156c of the opposing side edge 156 is shown fastened, i.e., forming a pants configuration. In FIG. 3, the second waist region 142 overlaps the first waist region 140 when they are fastened together.

The fasteners 172 may be formed of any material and in any form that will releasably attach to the mating surface of the opposing waist region when pressed against it. For example, the primary fastening component may be a mechanical fastener that releasably engages with the mating surface, such as by means of a plurality of hooks engaging with loops formed by fibers in a nonwoven sheet. Alternatively, the primary fastening component may be an adhesive that releasably adheres to the mating surface. In fact, the fasteners may include tape tabs, hook and loop fastening components, interlocking fasteners such as tabs & slots, buckles, buttons, snaps, and/or hermaphroditic fastening components. Exemplary surface fastening systems are disclosed in U.S. Pat. Nos. 3,848,594; 4,662,875; 4,846,815; 4,894,060; 4,946,527; 5,151,092; and 5,221,274, while an exemplary interlocking fastening system is disclosed in U.S. Pat. No. 6,432,098. The fastening system may also include primary and secondary fastening systems, as disclosed in U.S. Pat. No. 4,699,622. Additionally exemplary fasteners and fastener arrangements, the fastening components forming these fasteners, and the materials that are suitable for forming fasteners are described in U.S. Published Application Nos. 2003/0060794 and 2005/0222546 and U.S. Pat. No. 6,428,526.

Still other variations are also possible. For example, the fasteners 172 may be disposed on the interior of the article 120 in the first waist region 140 such that the first waist region 140 overlaps the second waist region 142 when they are fastened together. As another example, the fasteners 170 may be disposed on the exterior of the article 20 rather than on the interior. As a further example, the fasteners 170 may be used with a specific mating fastener surface particularly suited for cooperation with the fasteners 170 (e.g., a loop layer that works with a hook fastener, or a layer particularly treated to provide a suitable contacting surface for a specific adhesive).

Additional Variations to the Absorbent Article

In the alternative to the absorbent article 120 discussed above, various assemblies of topsheet 160, backsheet 162, and absorbent core 164 may be used. Additionally, the characteristics of the structures, the topsheet, for example, may be varied through the use of coatings, lotions, and the like. Further, in addition to the features described above, the disposable absorbent article 120 may include a variety of other features, such as slit openings, void spaces, leg cuffs, and the like to provide desired fit, containment, and aesthetic characteristics. Moreover, a transfer layer, which may also be referred to as an acquisition or distribution layer, or a sublayer may be disposed between the topsheet 160 and the core 164.

Thus, the topsheet, the backsheet, and the absorbent core may be assembled in the alternative in any of the well known configurations described in the following patent documents: U.S. Pat. Nos. 3,860,003; 5,151,092; 5,221,274; 5,554,145; 5,569,234; 5,580,411; and 6,004,306 (diapers) and U.S. Pat. Nos. 5,246,433; 5,569,234; 6,120,487; 6,120,489; 4,940,464; 5,092,861; 5,897,545; and 5,957,908 (pants).

The topsheet may be made from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet includes fibers, the fibers may be spunbond, carded, wet-laid, meltblown, hydroentangled, or otherwise processed as is known in the art. One such material, including staple-length polypropylene fibers, is the P-8 material commercially available from Veratec, Inc., a Division of International Paper Company, of Walpole, Mass. Other alternative topsheets are described in U.S. Pat. Nos. 3,929,135; 4,324,246; 4,342,314; 4,463,045; and 5,006,394. Still other alternative topsheets may be made in accordance with U.S. Pat. Nos. 4,609,518 and 4,629,643. Films that may be used to make alternative topsheets may include DRI-WEAVE film commercially available from The Procter & Gamble Company of Cincinnati, Ohio and CLIFF-T film from Tredegar Corporation of Richmond, Va.

In certain embodiments, at least a portion of the topsheet is made of a hydrophobic material or is treated to be hydrophobic in order to isolate the wearer's skin from liquids contained in the absorbent core. If the topsheet is made of a hydrophobic material, preferably at least a portion of the upper surface of the topsheet is treated to be hydrophilic so that liquids will transfer through the topsheet more rapidly. The topsheet can be rendered hydrophilic by treating it with a surfactant or by incorporating a surfactant into the topsheet. Suitable methods for treating the topsheet with a surfactant include spraying the topsheet material with the surfactant and/or immersing the material into the surfactant. A more detailed discussion of such a treatment and hydrophilicity is contained in, for example, U.S. Pat. Nos. 4,988,344 and 4,988,345. A more detailed discussion of some suitable methods for incorporating a surfactant in the topsheet may be found in U.S. Statutory Invention Registration No. H1670. Alternatively, the topsheet may include an apertured web or film which is hydrophobic. This may be accomplished by eliminating the hydrophilizing treatment step from the production process and/or applying a hydrophobic treatment to the topsheet, such as a polytetrafluroethylene compound like the SCOTCHGUARD product commercially available from 3M Corporation of Minneapolis, Minn., or a hydrophobic lotion composition. In such embodiments, it is preferred that the apertures be large enough to allow the penetration of aqueous fluids like urine without significant resistance.

Other materials may be applied or incorporated into the topsheet. For example, any portion of the topsheet may be coated with a lotion as is known in the art. Examples of suitable lotions include those described in U.S. Pat. Nos. 5,607,760; 5,609,587; 5,635,191; 5,643,588; 5,968,025 and 6,716,441. The lotion may function alone or in combination with another agent as the hydrophobizing treatment described above. The topsheet may also include or be treated with antibacterial agents, some examples of which are disclosed in PCT Publication No. WO 95/24173. Still other possibilities will be recognized.

The backsheet may be made from a thin plastic film, such as a thermoplastic film, having a thickness of about 0.012 mm (0.5 mil) to about 0.051 mm (2.0 mils). Exemplary backsheet films include the CPC2 film commercially available from Tredegar Corporation of Richmond, Va. Alternatively, the backsheet may be made from breathable materials, which materials permit vapors to escape from the absorbent article while still preventing bodily exudates from passing therethrough. Exemplary breathable materials may include woven webs, nonwoven webs, microporous films (such as ESPOIR NO film commercially available from Mitsui Toatsu Co. of Japan and EXAIRE film commercially available from Tredegar Corporation of Richmond, Va.), and monolithic films (such as HYTREL blend P18-3097 film commercially available from Clopay Corporation of Cincinnati, Ohio). Other alternative breathable materials may include composite materials, such as film-coated nonwoven webs or the composite materials described in PCT Publication No. WO 95/16746 and U.S. Pat. Nos. 5,938,648; 5,865,823; and 5,571,096.

The absorbent core may exhibit a wide variety of characteristics. For example, the core may be made in a wide variety of sizes and shapes (e.g., rectangular, hourglass, "T"-shaped, asymmetric, etc.). Further, the absorbent core may made from a wide variety of liquid-absorbent materials, such as those commonly used in disposable diapers and other absorbent articles, including comminuted wood pulp, which is generally referred to as airfelt. Other alternative absorbent materials may include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The configuration and structure of the absorbent core may also be varied: for example, the absorbent core(s) or other absorbent structure(s) may have varying caliper zones, hydrophilic gradient(s), superabsorbent gradient(s), or lower average density and lower average basis weight acquisition zones. Exemplary structures for use as the absorbent core may include those in U.S. Pat. Nos. 4,610,678; 4,673,402; 4,834,735; 4,888,231; 5,137,537; 5,147,345; 5,342,338; 5,260,345; 5,387,207; and 5,625,222.

The backsheet may be joined to the topsheet, the absorbent core or any other element of the absorbent article. In this fashion, the backsheet and the topsheet may be joined directly to each other in some locations and indirectly together in other locations, for example, by directly joining them to one or more other elements of the absorbent article 120. The attachment may be formed by any of a variety of attachment methods or mechanisms. For example, the attachment methods or mechanisms may include a uniform continuous layer of adhesive, a patterned layer of adhesive, or an array of separate lines, spirals, or spots of adhesive. One possible attachment mechanism includes an open pattern network of filaments of adhesive, as in U.S. Pat. No. 4,573,986. Another suitable attachment mechanism includes several lines of adhesive filaments which are swirled into a spiral pattern, as in U.S. Pat. Nos. 3,911,173; 4,785,996; and 4,842,666. Other adhesives which may be used are the HL-1620 and HL-1358-XZP adhesives commercially available from H. B. Fuller Company of St. Paul, Minn. Further alternative attachment mechanisms may include heat bonding, pressure bonding, ultrasonic bonding, dynamic mechanical bonding, or any other suitable attachment mechanism or combinations of these attachment mechanisms.

The topsheet may comprise one or more apertures to ease penetration of exudates therethrough, such as urine and/or feces (solid, semi-solid, or liquid). In sizing the primary aperture, it is appropriate to consider that, if the primary aperture is too small, the waste may not pass through the aperture, either due to poor alignment of the waste source and the aperture location or due to fecal masses having a diameter greater than the aperture. Likewise, if the aperture is too large, the area of skin that may be contaminated by "rewet" from the article is increased. Typically, the aperture should have an area of between about 10 cm$^2$ and about 50 cm$^2$. The aperture preferably has an area of between about 15 cm$^2$ and 35 cm$^2$.

Moreover, the absorbent article may also include pockets for receiving and containing waste, spacers which provide voids for waste, barriers for limiting the movement of waste in the article, compartments or voids which accept and contain waste materials deposited in the absorbent article 120, and the like, or any combinations thereof. Examples of pockets and spacers for use in absorbent products are described in U.S. Pat. Nos. 5,514,121; 5,171,236; 5,397,318; 5,540,671; 6,168,584; 5,306,266; and 5,997,520. Examples of compartments or voids are disclosed in U.S. Pat. Nos. 4,968,312; 4,990,147; 5,062,840; and 5,269,755. Exemplary structures, including elasticized or foreshortened topsheets, to provide a void space between the topsheet and the core are described in more detail in U.S. Pat. Nos. 4,892,536; 4,990,147; 5,037,416; and 5,269,775. Examples of suitable transverse barriers are described in U.S. Pat. Nos. 5,554,142 and 5,653,703; and PCT Publication No. WO 94/14395. Examples of other structures especially suitable for management of low viscosity feces are disclosed in U.S. Pat. Nos. 5,941,864; 5,977,430 and 6,013,063.

The absorbent article may include leg cuffs which provide improved containment of liquids and other body exudates. Leg cuffs may also be referred to as leg bands, side flaps, barrier cuffs, or elastic cuffs. Suitable cuffs may be described in U.S. Pat. Nos. 3,860,003; 4,808,178; 4,909,803; 4,695,278; and 4,795,454. In some embodiments, it may be desirable to treat all or a portion of the leg cuffs 32 with a lotion.

The absorbent article may also include a sublayer disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the diaper or may be one or more separate elements joined directly or indirectly with one or more elements of the diaper. Further, the sublayer may include a structure that is separate from the core or may include or be part of at least a portion of the core.

Suitable materials for use as the sublayer may include large cell open foams, macroporous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. One embodiment of a sublayer includes XPL-7124 mechanical fastening loop landing element, having an uncompressed thickness of about 1.5 millimeters, commercially available from the 3M Corporation of Minneapolis, Minn. Another embodiment includes a 6 denier, crimped and resin-bonded nonwoven highloft, having a basis weight of 110 grams per square meter and an uncompressed thickness of 7.9 millimeters, commercially available from The Glit Company of Wrens, Ga. Other suitable absorbent and non-absorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A stretch laminate comprising:
   (a) a first layer comprising an elastomer film, the first layer having a surface;
   (b) a second layer comprising a nonwoven material, the second layer having a surface that is attached to the surface of the first layer; and
   (c) a third layer comprising a nonwoven material, the third layer having a surface that is attached to the first layer on a surface opposite the second layer;
   wherein the first, second and third layers are bonded together by an attachment mechanism selected from the group consisting of heat bonding, pressure bonding, ultrasonic bonding, dynamic mechanical bonding and combinations thereof; and
   wherein the tensile behavior in the transverse direction of the stretch laminate is within about 2.5 N/cm of the tensile behavior in the transverse direction of the film at an engineering strain of about 1.5, and exists independent of mechanical activation.

2. The stretch laminate according to claim 1, wherein the tensile behavior in the transverse direction of the stretch laminate is within about 1 N/cm of the tensile behavior in the transverse direction of the film at an engineering strain of about 1.5.

3. The stretch laminate according to claim 1, wherein the laminate has an energy recovery value of 0.1 or higher for engineering strains between about 0.5 to about 2.5.

4. The stretch laminate according to claim 1, wherein the film has an energy recovery value of 0.1 or higher for engineering strains between about 1.5 and about 2.5.

5. The stretch laminate according to claim 1, wherein the attachment mechanism comprises ultrasonic bonding.

6. A method of making a stretch laminate, the method consisting essentially of:
(a) providing an elastomer film;
(b) attaching a first nonwoven layer to the elastomer film;
(c) attaching a second nonwoven layer to the elastomer film, the second layer being attached to the elastomer film on a surface opposite the first nonwoven layer;
wherein the attaching steps are accomplished via an attachment mechanism selected from the group consisting of heat bonding, pressure bonding, ultrasonic bonding, dynamic mechanical bonding and combinations thereof; and
wherein the tensile behavior in the transverse direction of the stretch laminate so made is within about 2.5 N/cm of the tensile behavior in the transverse direction of the film at an engineering strain of about 1.5, and exists independent of mechanical activation.

7. The method according to claim 6, wherein the tensile behavior in the transverse direction of the stretch laminate is within about 1 N/cm of the tensile behavior in the transverse direction of the film at an engineering strain of about 1.5.

8. The method according to claim 6, wherein the laminate has an energy recovery value of between 0.1 or greater for engineering strains between about 0.5 to about 2.5.

9. The method according to claim 6, wherein the film has an energy recovery value of 0.1 or greater for engineering strains between about 1.5 and about 2.5.

10. An absorbent article having a waist region and a crotch region, the article comprising:
(a) a backsheet having a longitudinal axis;
(b) a topsheet attached to the backsheet and having a body-facing surface, the topsheet comprising porous foams, reticulated foams, apertured plastic films, or woven or nonwoven materials of natural fibers, synthetic fibers, or a combination of natural and synthetic fibers;
(c) an absorbent core disposed between the backsheet and the topsheet; and
(d) a stretch laminate according to claim 1.

11. The absorbent article according to claim 10, wherein the tensile behavior in the transverse direction of the stretch laminate is within about 1 N/cm of the tensile behavior in the transverse direction of the film at an engineering strain of about 1.5.

12. The absorbent article according to claim 10, wherein the stretch laminate has an energy recovery value of 0.1 or higher for engineering strains between about 0.5 to about 2.5.

13. The absorbent article according to claim 10, wherein the elastomer film has an energy recovery value of 0.1 or higher for engineering strains between about 1.5 and about 2.5.

14. The absorbent article according to claim 10, wherein the waist region comprises the stretch laminate and the stretch laminate is attached to the backsheet.

15. The absorbent article according to claim 10, wherein the waist region comprises a side flap and comprises the stretch laminate, and the stretch laminate is attached to the backsheet.

16. The absorbent article according to claim 15, wherein a fastener is attached to the side flap.

17. The absorbent article according to claim 10, wherein the waist region comprises a side panel and comprises the stretch laminate, and the stretch laminate is attached to the backsheet.

18. The absorbent article according to claim 10, wherein the absorbent article is a diaper.

19. The absorbent article according to claim 10, wherein the absorbent article is a pant.

* * * * *